(12) United States Patent
Boothman

(10) Patent No.: US 10,070,995 B2
(45) Date of Patent: Sep. 11, 2018

(54) LEAKAGE-REDUCING DRESSING

(71) Applicant: KCI USA, Inc., San Antonio, TX (US)

(72) Inventor: Stuart Boothman, Keighley (GB)

(73) Assignee: KCI USA, INC., San Antonio, TX (US)

(*) Notice: Subject to any disclaimer, the term of this patent is extended or adjusted under 35 U.S.C. 154(b) by 427 days.

(21) Appl. No.: 14/856,692

(22) Filed: Sep. 17, 2015

(65) Prior Publication Data

US 2016/0074233 A1 Mar. 17, 2016

Related U.S. Application Data

(63) Continuation of application No. 13/641,376, filed as application No. PCT/GB2011/000589 on Apr. 15, 2011, now Pat. No. 9,192,521.

(30) Foreign Application Priority Data

Apr. 15, 2010 (GB) .................................. 1006323.8

(51) Int. Cl.
*A61F 13/02* (2006.01)
*A61F 13/56* (2006.01)
*A61F 13/00* (2006.01)

(52) U.S. Cl.
CPC ........ *A61F 13/0223* (2013.01); *A61F 13/022* (2013.01); *A61F 13/0203* (2013.01);
(Continued)

(58) Field of Classification Search
CPC .............. A61F 13/0203; A61F 13/0206; A61F 13/0213; A61F 13/022; A61F 13/0223;
(Continued)

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Lynne Anderson

(74) *Attorney, Agent, or Firm* — Foley & Lardner LLP

(57) ABSTRACT

An adhesive dressing that reduces the leakage of wound exudate from the dressing, comprising an adhesive-coated backing sheet; and an absorbent island adhered to said adhesive-coated backing sheet by said adhesive, having a first end and a second end, wherein the absorption capacity of the absorbent island is higher at the first end than at the second end. The adhesive dressing of the invention provides extended wear time for the dressing when it is applied to wounds.

39 Claims, 5 Drawing Sheets

(52) U.S. Cl.
CPC ........ *A61F 13/025* (2013.01); *A61F 13/0206* (2013.01); *A61F 13/56* (2013.01); *A61F 2013/00578* (2013.01); *A61F 2013/00612* (2013.01); *A61F 2013/00731* (2013.01)

(58) Field of Classification Search
CPC ................ A61F 13/0226; A61F 13/025; A61F 2013/00578; A61F 2013/00612; A61F 2013/00731
See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,319,238 B1 * | 11/2001 | Sartorio ............ A61F 13/47209 604/330 |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 9,192,521 B2 * | 11/2015 | Boothman ........ A61F 13/0203 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2003/0125680 A1 * | 7/2003 | Ding .................. A61F 13/0203 604/304 |
| 2012/0123312 A1 * | 5/2012 | Tai ...................... A61F 13/068 602/54 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |

(56) References Cited

FOREIGN PATENT DOCUMENTS

| WO | 97/18007 A1 | 5/1997 |
|---|---|---|
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax,"Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

* cited by examiner

LEAKAGE-REDUCING DRESSING

The invention relates to wound dressings, especially adhesive island-type wound dressings, and in particular to dressings that exhibits reduced leakage of exudate in use.

Adhesive dressings are known for the treatment of wounds, including ulcers and pressure sores. Typical adhesive dressings are the so-called island dressings, in which an area of absorbent wound dressing material (the island) is supported on a larger, adhesive-coated, suitably microorganism-resistant backing sheet that provides an adhesive-coated margin around the island. The absorbent island is normally of symmetrical shape, that is to say it normally has at least two-fold rotational symmetry about an axis perpendicular to the plane of the dressing through a central point in the island, for example it may have a generally round, square, oval or rectangular shape. The absorbent island is usually fully oriented with, and centred on, a similarly shaped backing sheet shape so as to provide an adhesive margin of substantially uniform width around the island.

In practice, most wounds are inclined at least in part at an angle to the horizontal plane. This applies especially to leg and trunk wounds in ambulatory patients. Standard adhesive island dressings, when applied to such wounds, can exhibit leakage at the bottom of the dressing even when a volume of exudate less than the maximum absorbency of the island has been exuded from the wound, because the wound exudate tends to collect under gravity in the lower part of the absorbent island in use, and from there to leak out of the bottom of the dressing. WO2008/149107 discloses an example of an adhesive dressing used on a contoured area of the body. CN201179151 discloses dressings suitable for use on fingers.

Bandages that may be cut to size are known in the art. US2004/0049144 discusses hypoallergenic bandages wherein a portion of the backing sheet has a triangular shape.

The present invention is based on the principle devised by the present inventors that the frequency of dressing failure and change of dressing can be reduced by providing an island-type dressing having a first end and a second end, wherein the absorption capacity of the island is higher at the first end than at the second end, such that the first end is positioned lowermost in use.

In a first aspect, the invention provides an adhesive dressing comprising an adhesive-coated backing sheet; and an absorbent island adhered to said backing sheet by said adhesive, said island in plan view having a first end and a second end, wherein the absorption capacity of the absorbent island is higher at the first end than at the second end.

The characterizing feature of the dressings according to the present invention is the use of an absorbent island having increased absorption capacity at one end. The absorbent island is suitably in the form of a substantially continuous sheet, comprising one or more layers, and having a periphery defining edges of the island. One of these edges will form the top edge of the island in use (i.e. will be located uppermost on the patient in use), and an opposite edge will form the bottom edge of the island in use. The term "first end of the island" herein refers to a region proximate to, and including, the bottom edge of the island. The term "second end of the island" herein refers to a region proximate to, and including, the top edge of the island. The first end is suitably divided from the second end by a straight line drawn perpendicular to the mid-point of a straight line drawn between the top edge and the bottom edge, whereby the areas of the first and second ends together make up the whole area of the island.

The term "absorption capacity" refers to the volume of wound exudate that the material comprising the island may absorb before it is saturated. The absorption capacity of any defined region of the absorbent island is the volume of wound exudate that the material comprising that region of the island may absorb when it is saturated. This may be measured as millilitres of physiological saline solution at 25 C absorbed by the uncompressed island material in the said region upon immersion in excess physiological saline solution for 30 seconds followed by draining.

It will be apparent that the different absorption capacities of the first and second ends may be achieved generally in any of the following ways. The first end may be made of a more absorbent material than the second end, and/or the first end may have greater thickness than the second end, and/or the first end may have a greater area than the second end. Preferably, the absorption capacity increases continuously from the second end to the first end, and may increase linearly from the second end to the first end.

For example, the first end may incorporate a higher fraction of superabsorbent particles or fibers than the second end of the island, typically by means of a concentration gradient of the superabsorbent from the second end to the first end. In practice, these embodiments could be relatively difficult to manufacture.

Alternatively or additionally, the volume of material comprising the absorbent island is greater at the first end than at the second end. In certain embodiments, this may be achieved by making the thickness of the absorbent island greater at the first end than at the second end. In these embodiments, the thickness of the island may increase continuously from the top edge to the bottom edge, and it may increase linearly from the top edge to the bottom edge. In other embodiments, the first end of the island may comprise one or more additional layers of absorbent material that are not present in the second end.

However, for ease of manufacturing the most suitable method is to shape the island so that the first end has a larger area than the second end. Suitably, the composition of the one or more layers making up the island is uniform between the first end and the second end, and the difference in absorption capacity is achieved only by making the areas of the two ends different.

In embodiments, the absorbent island suitably does not have any rotational symmetry about an axis perpendicular to the island, unlike previous island dressings. The absorbent island in the dressings of the present invention may still suitably have rotational symmetry about an axis that bisects the island in the plane of the island and that runs from the first edge to the second edge perpendicular to the dressing plane (C2 symmetry). Suitable shapes of this type for the absorbent island include triangular, trapezoidal, dome-shaped, pear-shaped and bell-shaped. Any of these shapes may have rounded or chamfered vertices. Trapezoidal shapes are especially suitable. Preferably, the absorbent island is not t-shaped.

Suitably, the respective bottom and top edges at the first and second ends of the absorbent island are substantially linear and substantially parallel. Suitably, the length of the bottom edge is from 1.2 to 3 times the length of the top edge.

In any event, the absorbent capacity of the first end of the absorbent island is suitably from about 1.1 to 10 times the absorbent capacity of the second end, more suitably from about 1.3 to 5 times, and most suitably from about 1.5 to 2 times.

In relation to the present invention, "bottom" and "top" are relative terms signifying the first end and the second end of the adhesive dressing intended respectively to be located uppermost and lowermost in use The absorbent island may comprise any of the layers conventionally used for absorbing wound fluids, serum or blood in the wound healing art, including gauzes, nonwoven fabrics, superabsorbents, hydrogels and mixtures thereof. Suitably, the absorbent island comprises a layer of hydrophilic polyurethane foam, such as an open celled hydrophilic polyurethane foam prepared in accordance with EP-A-0541391. The absorbent island may further comprise a wicking layer. This may be a layer of a nonwoven fibrous web, for example a carded web of viscose staple fibers. The basis weight of the absorbent layer may be in the range of 50-500 g/m$^2$, such as 100-400 g/m$^2$. The uncompressed thickness of the absorbent layer may be in the range of from 0.5 mm to 10 mm, such as 1 mm to 4 mm. The free (uncompressed) liquid absorbency measured for physiological saline may be in the range of 5 to 30 g/g at 25° C. The absorbent island may comprise a layer of such absorbent material enclosed or covered by a liquid-permeable film or sheet, such as a perforated thermoplastic film. The composition of the absorbent material may vary to give greater absorbency at the first end.

The area of the absorbent island is typically in the range of from 1 cm$^2$ to 400 cm$^2$, more suitably from 4 cm$^2$ to 200 cm$^2$, still more suitably from about 10 cm$^2$ to about 150 cm$^2$, for example from about 16 cm$^2$ to about 100 cm$^2$. Dressings of this size are especially suitable for the treatment of leg ulcers.

The absorbent island may be covered on its wound-facing side by a liquid-permeable wound contacting sheet (top sheet), such as a non-adherent perforated plastic film. Suitably, the wound facing surface of the absorbent island itself is substantially free of the adhesive present on the backing sheet.

The adhesive-coated backing sheet may have any shape, such as square, rectangular, circular, oval, trapezium-shaped, suitably with rounded corners. In suitable embodiments, the backing sheet may have substantially the same shape as the absorbent island, e.g. it may be triangular, trapezoidal, dome-shaped, pear-shaped and bell-shaped. This allows the provision of an adhesive margin of substantially constant width around the island, and also makes correct orientation of the dressing on the patient straightforward as it is immediately apparent which end of the dressing should be located lowermost.

The island has a smaller area than the adhesive-coated backing sheet such that an adhesive-coated margin of the backing sheet extends around the island. Preferably, the adhesive-coated margin extends around every edge of the absorbent island. Suitably, the adhesive-coated margin has a mean width of from 0.5 to 5 cm, suitably from 1 to 3 cm. In order to minimise dressing leakage, the width of the adhesive-coated margin may be wider at the first end of the absorbent island than at the second end of the absorbent island. For example, the width of the adhesive-coated margin may be wider adjacent to the first end of the absorbent island than adjacent to the second edge of the absorbent island by 20%, 50% or 100%.

The adhesive-coated backing sheet supports the absorbent island and suitably provides a barrier to passage of microorganisms through the dressing. Suitably, the adhesive-coated backing sheet is substantially liquid-impermeable. The adhesive-coated backing sheet is suitably semipermeable. That is to say, the adhesive-coated backing sheet is suitably permeable to water vapour, but not permeable to liquid water or wound exudate. Suitably, the adhesive-coated backing sheet is also microorganism-impermeable. Suitable continuous conformable adhesive-coated backing sheets will suitably have a moisture vapor transmission rate (MVTR) of the backing sheet alone of 300 to 5000 g/m$^2$/24 hrs, suitably 500 to 2000 g/m$^2$/24 hrs at 37.5° C. at 100% to 10% relative humidity difference. The adhesive-coated backing sheet thickness is suitably in the range of 10 to 1000 micrometers, more suitably 100 to 500 micrometers.

Suitable polymers for forming the adhesive-coated backing sheet include polyurethanes and poly alkoxyalkyl acrylates and methacrylates such as those disclosed in GB-A-1280631. Suitably, the adhesive-coated backing sheet comprises a continuous layer of a high density blocked polyurethane foam that is predominantly closed-cell. A suitable adhesive-coated backing sheet material is the polyurethane film available under the Registered Trade Mark ESTANE 5714F. Also suitable are elastomeric polymeric esters such as Du Pont HYTREL (Registered Trade Mark).

Suitably, the backing sheet may feature indicia signifying that the first end should be positioned lowermost in use. For example, the indicia may signify that the first end of the adhesive dressing is the "bottom" and that the second end of the adhesive dressing is the "top". The indicia may be printed or embossed on the surface of the backing sheet opposite the absorbent island.

The adhesive should suitably be moisture vapor transmitting and/or patterned to allow passage of water vapor therethrough. The adhesive layer is suitably a continuous moisture vapor transmitting, pressure-sensitive adhesive layer of the type conventionally used for island-type wound dressings, for example, a pressure sensitive adhesive based on acrylate ester copolymers, polyvinyl ethyl ether and polyurethane as described for example in GB-A-1280631. The basis weight of the adhesive layer is suitably 20 to 250 g/m$^2$, and more suitably 50 to 150 g/m$^2$. Polyurethane-based pressure sensitive adhesives are suitable.

The adhesive dressing according to the present invention may further comprise at least one removable cover sheet to cover the absorbent island and the adhesive-coated margin of the backing sheet around the absorbent island. The cover sheet covers and protects the absorbent island and prevents premature adhesion of the adhesive layer. The cover sheet is removed by the care giver immediately before application of the dressing.

The cover sheet may comprise a film of polyethylene, polypropylene or fluorocarbons and papers coated with these materials. Suitably, the cover sheet is a release-coated paper sheet, such as a silicone release-coated paper sheet. Examples of silicone-coated release papers are POLYSLIK (Registered Trade Mark) supplied by H.P. Smith & Co., offered in various formulations to control the degree of adhesion of the paper to the adhesive surface.

Suitably, the dressing comprises a first removable cover sheet having a first edge and a second removable cover sheet that meets the first cover sheet along the first edge, wherein the first edge extends along a line substantially from the top edge of the absorbent layer to the bottom edge of the absorbent layer.

The directional alignment of the cover sheet edges can be helpful to assist the care giver in achieving accurate alignment of the absorbent layer with the area to be treated. For this reason, suitably at least one of the edges along which the cover sheets meet is substantially straight.

Certain suitable dressings have a central cover sheet with first and second opposed edges, and two side cover sheets that meet the central cover sheet along the opposed edges. Suitably, the opposed edges are substantially parallel. This arrangement of three cover sheets is especially suitable for positioning of relatively large dressings, such as sacral dressings, as described in detail in EP-A-0117632.

Suitably, along each of said edges where the cover sheets meet, one of the cover sheets is folded back to provide a folded-back margin, and the other cover sheet overlaps the said folded-back margin. This provides an easy-to-grasp margin on each cover sheet in the region of overlap to assist removal of the cover sheets by the care giver.

In the case of the embodiment comprising three cover sheets described above, each side cover sheet is suitably folded back along each of said edges where the cover sheets meet to provide a folded-back margin, and the central cover sheet overlaps the said folded-back margin, suitably as described in EP-A-0117632.

Suitably, at least one of the edges along which the cover sheets meet is substantially parallel or perpendicular to the long axis of the island. This enables the care giver to orient the absorbent island in position by reference to the cover sheets without reference to the backing sheet. This is especially useful when the backing sheet is not transparent or translucent.

In the adhesive dressing of the invention, the time to failure of the dressing is increased compared with an adhesive dressing wherein the absorbent island has uniform absorbency throughout. Failure of the dressing is identified by the leakage of wound exudate outside of the area of the absorbent island.

Suitably, the adhesive dressing according to the present invention is a leg ulcer wound dressing.

Suitably, the adhesive dressing according to the present invention is suitable for medical use. Suitably the dressing is sterile and packaged in a microorganism-impermeable container.

The present invention is also directed to the use of the adhesive dressings as described herein in a method of treating a subject in need thereof comprising applying the adhesive dressing to the body of the subject. The present invention further relates to the use of the adhesive dressings as described herein in a method of treating a wound in a subject in need thereof comprising applying the adhesive dressing to the wound. The dressing is applied by adhesion of the margin around the wound to cover the wound. The dressing is applied suitably for a period of from 30 minutes to about 72 hours, for example from about 1 hour to about 48 hours, or until saturated with wound fluid.

Embodiments of the present invention will now be described further, by way of example, with reference to the accompanying drawings, in which:

FIG. 1a shows a bottom plan view of an adhesive dressing according to the a first embodiment of the present invention. FIG. 1b shows a profile view of the same dressing. FIG. 1c shows a top plan view of the same dressing.

FIG. 2a shows a bottom plan view of a second embodiment of the adhesive dressing of the present invention. FIG. 2b shows a profile view of the same embodiment. FIG. 2c shows a perspective bottom view of the same dressing with cover sheets over the adhesive layer and absorbent island.

Embodiments of the present invention will now be described by way of example with reference to the accompanying drawings.

Figure 1A:
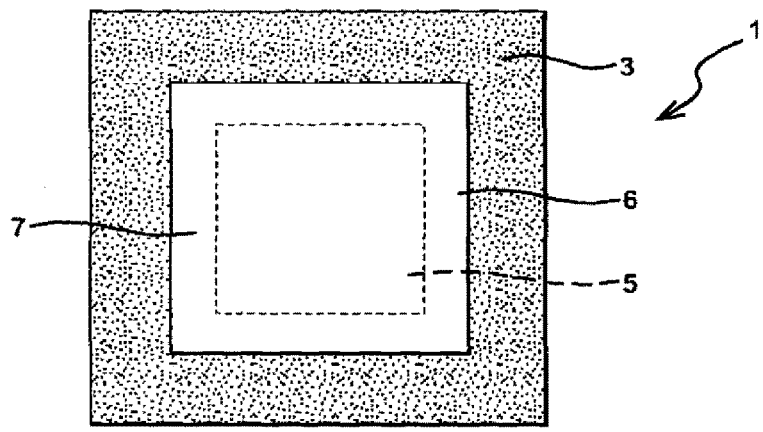

Referring to FIG. 1, the adhesive dressing 1, which is an embodiment of the present invention, is an island-type adhesive wound dressing comprising a rectangular backing layer 2 of microporous liquid-impermeable polyurethane foam, such as ESTANE 5714F (Registered Trade Mark). The backing layer is permeable to water vapor, but impermeable to wound exudate and microorganisms.

The backing layer 2 is coated with a substantially continuous layer of pressure-sensitive polyurethane adhesive 3. An absorbent island 4 is adhered to a central region of the adhesive-coated backing sheet 1.

The absorbent island 4 comprises a highly absorbent wicking layer 5 covered by a wound-contacting top layer 6 that extends over and beyond the edges of the highly absorbent layer 5 so that edges 7 of the top layer 6 are adhered to the adhesive layer and enclose the highly absorbent layer 5. The top layer is formed of hydrophilic polyurethane foam prepared as described in EP-A-0541391 and having a basis weight of about 350 g/m$^2$ and a thickness of about 1.5 mm. The highly absorbent layer 5 is formed from a nonwoven fabric of mixed viscose and superabsorbent fibers sold under the registered trade mark OASIS.

Figure 1B:
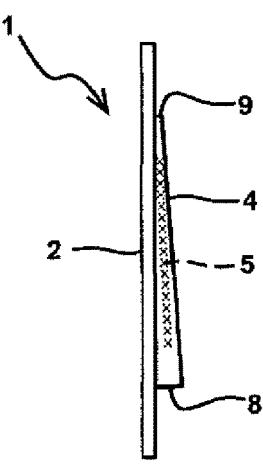
Figure 1C:
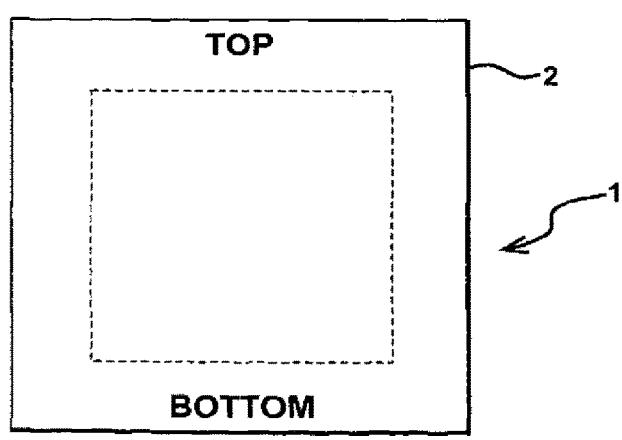

The thickness of the absorbent island is greater at the first end 8 than at the second end 9, as shown in FIG. 1b. For a typical leg ulcer dressing, the area of the absorbent island is approximately 50 cm$^2$ and the width of the adhesive-coated margin is approximately 2 cm. In order to assist correct placement of the dressing, the surface of the backing sheet opposite to the absorbent layer is printed with indicia TOP and BOTTOM as shown in FIG. 1c to indicate which end of the dressing (i.e. the end corresponding to the most absorbent, thickest end of the absorbent island) is to be located lowermost in use.

Figure 2A:
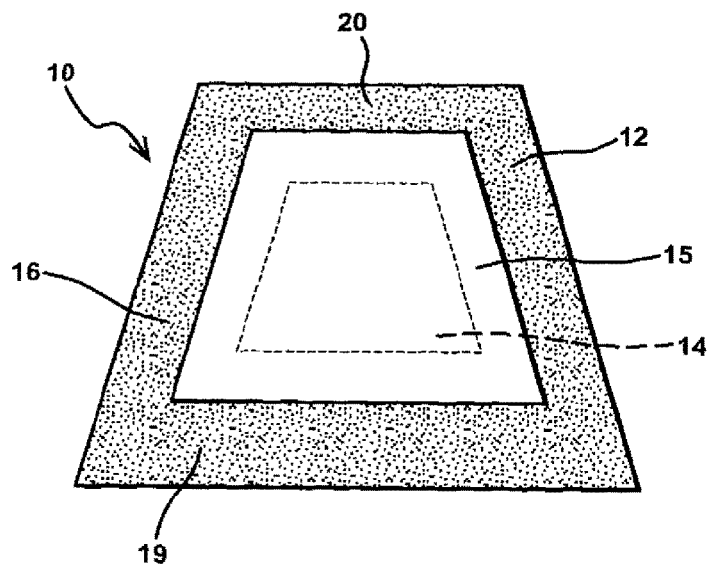
Figure 2B:
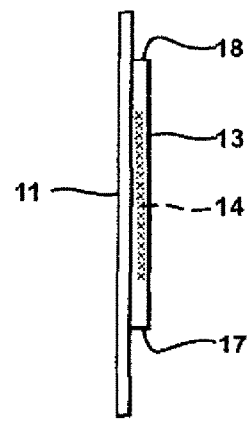

Referring to FIG. 2, the adhesive dressing 10 is an island-type adhesive wound dressing comprising a backing layer 11 of microporous liquid-impermeable polyurethane foam, such as ESTANE 5714F (Registered Trade Mark). The backing layer is permeable to water vapor, but impermeable to wound exudate and microorganisms. The backing layer is trapezium-shaped.

The backing layer 11 is coated with a substantially continuous layer of pressure-sensitive polyurethane adhesive 12. An absorbent island 13 is adhered to a central region of the adhesive-coated backing sheet 11. The absorbent island is also trapezium shaped. The shape of the absorbent island is the same as that of the backing layer 11 but the dimensions are smaller.

The absorbent island 13 comprises a trapezium-shaped highly absorbent layer 14 covered by a trapezium-shaped wound contacting top layer 15 that extends over and beyond the edges of the highly absorbent layer 14 so that edges 16 of the top layer 15 are adhered to the adhesive layer and enclose the highly absorbent layer 14. The top layer is formed of hydrophilic polyurethane foam prepared as described in EP-A-0541391 and having a basis weight of about 350 g/m² and a thickness of about 1.5 mm. The highly absorbent layer 14 is formed from a nonwoven fabric of mixed viscose and superabsorbent fibers sold under the registered trade mark OASIS.

For a typical leg ulcer dressing, the area of the absorbent island is approximately 50 cm² and the width of the adhesive-coated margin adjacent the top edge and sides of the island is approximately 2 cm. The width of the adhesive margin 19 adjacent the bottom edge of the trapezium is greater than the adhesive margin 20 at the narrower edge of the trapezium, for example the margin 19 may have a width of 3-4 cm.

Figure 2C:
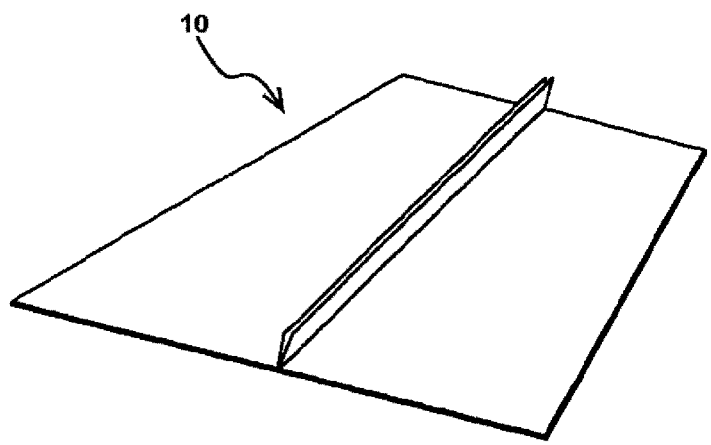

The wound facing surface of the dressings shown in FIGS. 1 and 2 is protected by release papers before use, as shown in FIG. 2c. The dressing may be packaged in a microorganism-impermeable pouch (not shown), and sterilised using gamma radiation.

Figure 3A:
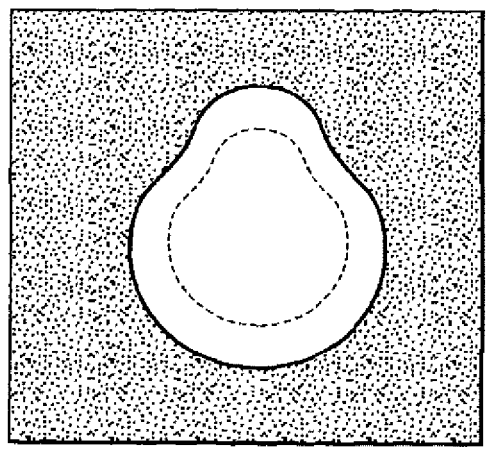
FIGS. 3a, 3b and 3c show bottom plan views of three further embodiments of the invention.
Figure 3B:
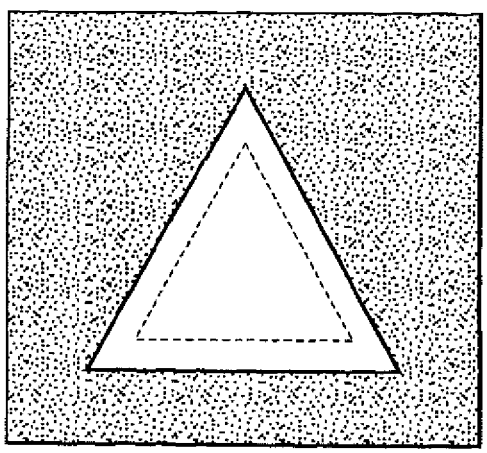
Figure 3C:
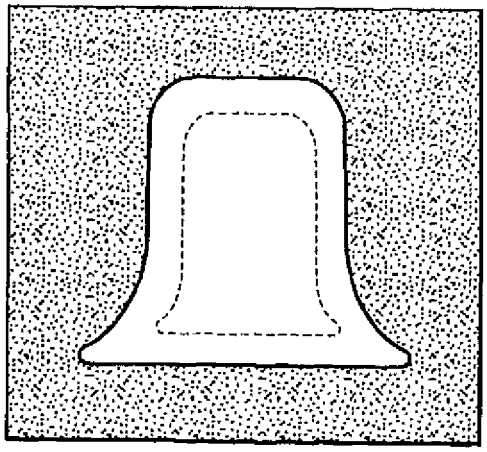

Referring to FIG. 3, three alternative embodiments are shown having, respectively, pear-shaped, triangular and bell-shaped absorbent islands on a rectangular backing sheet.

EXAMPLES

Working Example and Comparative Example

A trapezium-shaped leakage reducing dressing was prepared as shown in FIG. 2, in which the length of the bottom of each component was 1.75 times longer than the top, whereby the shape of each component was substantially identical. The dimensions of the leakage-reducing dressing were calculated so that the area of each component of the dressing are equal to the comparative standard square dressing. The comparative standard square dressing has dimensions the same as those of the leakage-reducing dressing of FIG. 1 but has an absorbent island of uniform thickness. In order to allow the dimensions to be rounded up to one that is easily measurable there was a slight difference in the size of the island polyurethane foam hydropolymer layer (standard 51.84 cm²; leakage reducing 52.77 cm²) and the wicking layer (standard 25.00 cm²; leakage reducing 24.75 cm²). Hydropolymer weights were measured for each set of dressings to ensure that a difference in hydropolymer thickness or density would not result in a difference in performance: the mean average weight of hydropolymer in the comparative standard dressing was 1.91 g and for the leakage reducing dressing according to the invention it was 1.86 g.

Simulation

Simulated leg model apparatus was constructed from a peristaltic pump, tubing, and a tall measuring cylinder which simulates the patient's leg. The peristaltic pump delivered a flow of simulated wound fluid (saline, albumin and blue dye) through tubing which is threaded through a hole in the measuring cylinder. The end of the tubing is flush to the front surface of the cylinder. A small filter paper (42.5 mm in diameter) is centrally placed over the end of the tubing to disperse the flow of the wound fluid over the area of the paper to simulate a wound of this size. Six leg models were used to test 6 samples simultaneously, the flow rate of each leg model is determined by weighing the quantity of fluid pumped through the tubing over a set time period. A small degree of variation typically exists between the flow rates of each model, but all subsequent calculations take this variation into account. Fluid is delivered to the dressings until the dressing fails; this is identified by leakage of the simulated wound fluid outside of the absorbent island. The amount of fluid absorbed by the dressing was then determined by multiplying the flow rate by the time of the dressing was on the model up to failure.

Flow Rate Calibration

Although exudate production by wounds can vary greatly depending on factors such as wound size and infection, 0.5 ml per hour is considered to be reasonable representation of chronic wound exudate production. The flow rate of each leg model is determined by weighing the quantity of fluid pumped over a set time period (5 h). A small degree of variation between the flow rates of the leg models was observed and accounted for in all calculations.

TABLE 1

Flow rate calibration data

| Model no | Start weight (g) | End weight (g) | Fluid delivered in 5 h (ml) | Flow rate (ml/h) |
|---|---|---|---|---|
| 1 | 47.0890 | 49.4110 | 2.3220 | 0.4644 |
| 2 | 79.6250 | 81.9032 | 2.2782 | 0.4556 |
| 3 | 74.4340 | 81.8339 | 2.3999 | 0.4800 |
| 4 | 80.6201 | 82.8739 | 2.6138 | 0.5228 |
| 5 | 79.4936 | 82.1277 | 2.6341 | 0.5268 |
| 6 | 83.3020 | 85.9321 | 2.6301 | 0.5260 |

Comparison of Fluid Absorption Prior to Leakage (Failure)

Three testing runs were completed using six models; 9 standard dressings were assessed in comparison with 6 leakage reducing dressings of the present invention and 3 upside-down leakage reducing dressings of the present invention.

TABLE 2

Amount of fluid absorbed by wound dressings prior to failure

| | Standard Dressing | | | |
|---|---|---|---|---|
| | Model 1 | Model 2 | Model 3 | |
| Replicate 1 | | | | |
| Time to failure leakage (h) | 14.5 | 15 | 19.5 | |
| Flow rate (ml/h) | 0.4644 | 0.4556 | 0.48 | |
| Total fluid | 6.73 | 6.83 | 9.36 | Mean 7.64 ml |
| Replicate 2 | | | | |
| Time to failure leakage (h) | 15.5 | 13 | 12 | |
| Flow rate (ml/h) | 0.4644 | 0.4556 | 0.4800 ml per hour | |
| Total fluid | 7.20 | 5.92 | 5.76 | Mean 6.29 ml |
| Total mean | 6.97 ml | SD | 1.30 | |
| | Trapezium Dressing | | | |
| | Model 4 | Model 5 | Model 6 | |
| Replicate 1 | | | | |
| Time to failure leakage (h) | 18 | 16 | 21.75 | |
| Flow rate (ml/h) | 0.5228 | 0.5268 | 0.526 | |
| Total fluid | 9.41 | 8.43 | 1.44 | Mean 9.76 ml |
| Replicate 2 | | | | |
| Time to failure leakage (h) | 17 | 15 | 16 | |
| Flow rate (ml/h) | 0.5228 | 0.5268 | 0.526 | |
| Total fluid | 8.89 | 7.90 | 8.42 | Mean 8.40 ml |
| Total mean | 9.08 ml | SD | 1.26 | |

TABLE 2-continued

Amount of fluid absorbed by wound dressings prior to failure

| | Standard Dressing | | | |
| --- | --- | --- | --- | --- |
| | Model 1 | Model 2 | Model 3 | |
| Replicate 1 | | | | |
| Time to failure leakage (h) | 13.75 | 16.5 | 12 | |
| Flow rate (ml/h) | 0.4644 | 0.4556 | 0.48 | |
| Total Fluid | 6.39 | 7.52 | 5.76 | Mean 6.55 ml |
| | Trapezium Dressing (upside down) | | | |
| | Model 4 | Model 5 | Model 6 | |
| Replicate 1 | | | | |
| Time to failure leakage (h) | 12.75 | 12.33 | 13 | |
| Flow rate (ml/h) | 0.5228 | 0.5268 | 0.526 | |
| Total Fluid | 6.67 | 6.50 | 6.84 | Mean 6.67 ml |

Figure 4:
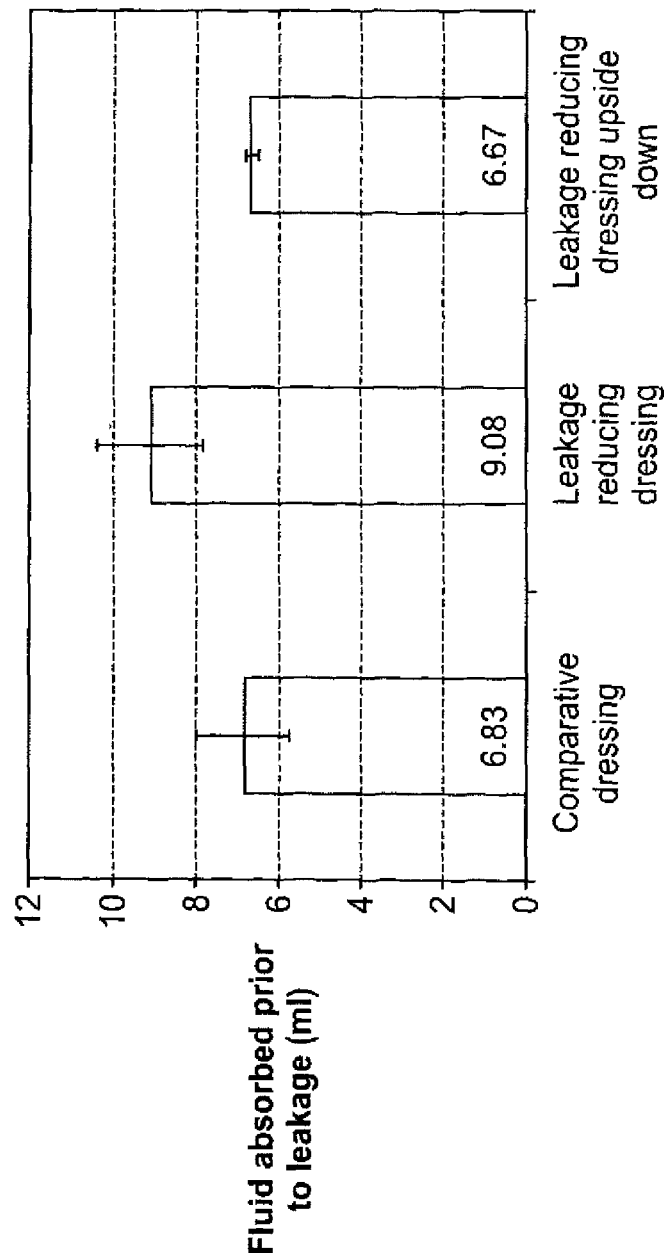
FIG. 4 shows a bar chart of the volume of simulated wound fluid absorbed prior to leakage for a standard dressing according to the prior art and for a leakage-reducing adhesive dressing of the present invention, when used in two different orientations.

As shown in FIG. 4, the leakage reducing dressing absorbed a greater volume of simulated wound fluid prior to leakage compared to the comparative standard dressing (9.08 ml vs 6.83 ml, respectively), demonstrating that the trapezium shape increases the absorption of fluid under the effect of gravity. Placing the leakage reducing dressing upside down negated this effect and fluid absorption levels were comparable with the comparative standard dressing (6.67 ml). The difference in absorbency between the comparative standard dressing and the leakage reducing dressing is statistically significant ($p=0.003$).

Visual Comparison of Fluid-handling Capacity

Figure 5:
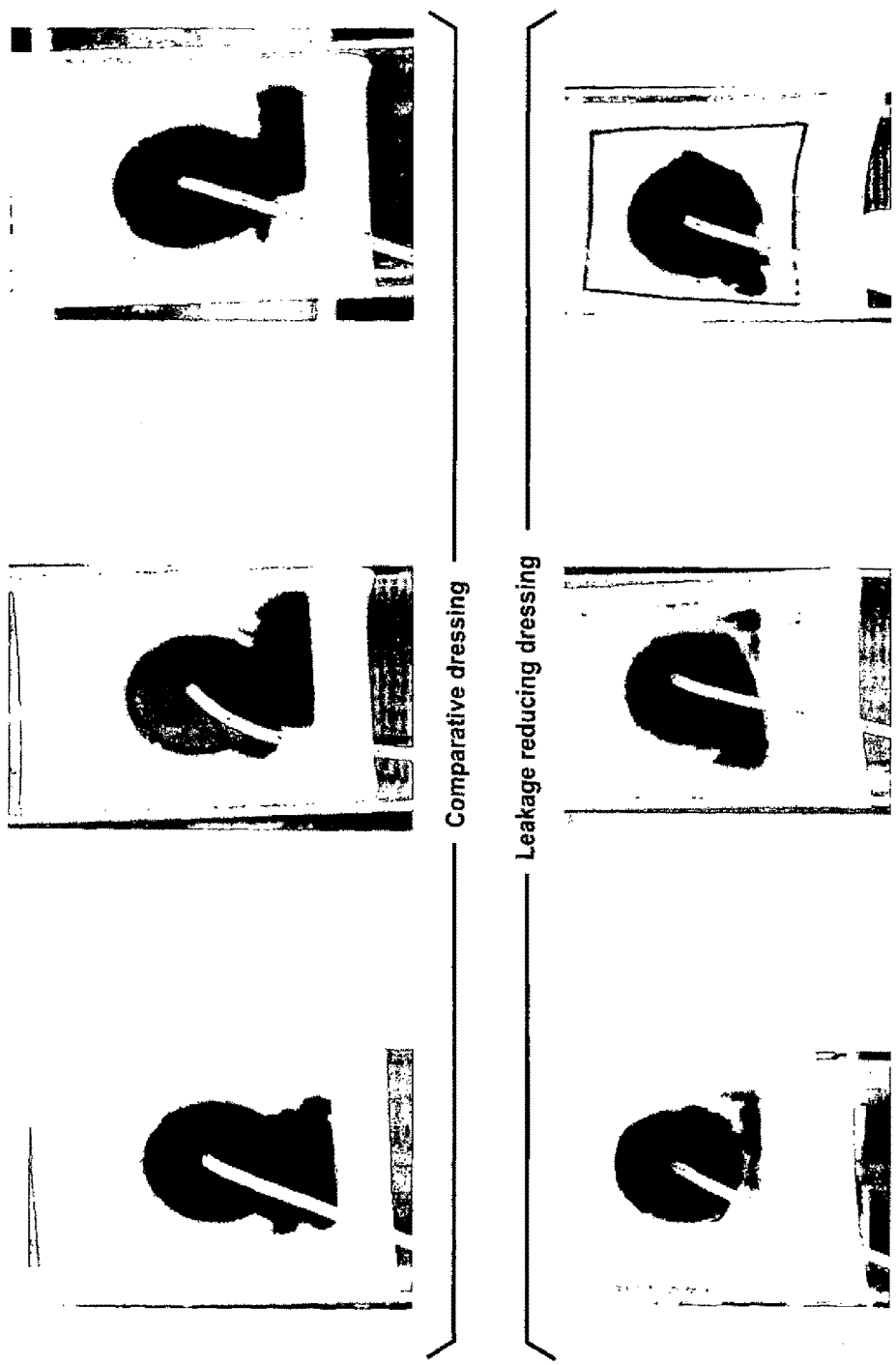
FIG. 5 shows photographs of a simulation of wound fluid being absorbed by a standard dressing according to the prior art and by a leakage reducing adhesive dressing of the present invention.

The use of dye in the simulated wound fluid allows the passage of the fluid movement to be tracked (see FIG. 5). It is apparent from FIG. 5 that fluid does not reach the upper part of the dressing and this area of the dressing is not effectively used. A standard adhesive dressing has the potential to absorb 25 ml of fluid when fully saturated, However, when tested under the effect of gravity, it only absorbs approximately 25% of that volume. The trapezium shape of the leakage reducing dressing confers greater fluid handling capacity in its lower half, extending the wear time of this dressing by over 30% and reducing the risk of premature dressing failure.

The above embodiments have been described by way of example only It is understood that many other embodiments falling within the scope of the accompanying claims will be apparent to the skilled reader. All publications, patents, and patent applications cited herein are hereby incorporated by reference in their entirety for all purposes.

The invention claimed is:

1. An adhesive dressing comprising:
   a backing sheet comprising an adhesive coating; and
   an absorbent island attached to said backing sheet, said absorbent island having a first end and a second end;
   wherein a width of an adhesive margin is greater in a region of said margin adjacent to the first end of the absorbent island than in a region of said margin adjacent to the second end of the absorbent island; and
   wherein the absorption capacity of the absorbent island is higher at the first end than at the second end.

2. The adhesive dressing of claim 1, wherein the volume of material comprising the absorbent island is greater at the first end than at the second end.

3. The adhesive dressing of claim 1, wherein the first end of the absorbent island is wider than the second end.

4. The adhesive dressing of claim 3, wherein the absorbent island has a periphery defining top and bottom edges of said island and said top and bottom edges of the absorbent island are substantially straight and substantially parallel.

5. The adhesive dressing of claim 3, wherein the first end of the absorbent island is from about 1.1 to about 3 times wider than the second end.

6. The adhesive dressing of claim 1, wherein the absorbent island is substantially triangular, trapezium-shaped, dome-shaped, bell-shaped or pear-shaped.

7. The adhesive dressing of claim 6, wherein the backing sheet has substantially the same shape as the absorbent island.

8. The adhesive dressing of claim 1, wherein the thickness of the absorbent island is greater at the first end than at the second end.

9. The adhesive dressing of claim 8, wherein the thickness of the absorbent island increases continuously from the second end to the first end.

10. The adhesive dressing of claim 1, wherein the area of the absorbent island is from about 10 cm$^2$ to about 100 cm$^2$.

11. The adhesive dressing of claim 1, wherein the absorbent island comprises a layer of a hydrophilic polyurethane foam.

12. The adhesive dressing of claim 11, wherein the absorbent island further comprises a wicking layer.

13. The adhesive dressing according to claim 1, wherein a surface of the backing sheet opposite said absorbent island comprises indicia identifying an edge of the dressing that should be positioned lowermost in use.

14. The adhesive dressing of claim 1, wherein the absorbent island is attached to the backing sheet within the adhesive margin provided by the backing sheet, the adhesive margin extending entirely around the absorbent island.

15. The adhesive dressing of claim 4, wherein the first end of the absorbent island is from about 1.1 to about 3 times wider than the second end.

16. A method of treating a wound, comprising:
    applying an adhesive dressing having an adhesive-coated backing sheet and an absorbent island attached to the backing sheet to a wound site such that a first end of the absorbent island is below a second end of the absorbent island when the wound is in its most often-occurring orientation;
    wherein a width of an adhesive margin is greater in a region of said margin adjacent to the first end of the absorbent island than in a region of said margin adjacent to the second end of the absorbent island; and
    wherein the first end of the absorbent island has a greater absorbent capacity than a second end of the absorbent island.

17. The method of claim 16, wherein the volume of material comprising the absorbent island is greater at the first end than at the second end.

18. The method of claim 16, wherein the first end of the absorbent island is wider than the second end.

19. The method of claim 16, wherein the absorbent island is substantially triangular, trapezium-shaped, dome-shaped, bell-shaped, or pear-shaped.

20. The method of claim 16, wherein the thickness of the absorbent island is greater at the first end than at the second end.

21. The method of claim 20, wherein the thickness of the absorbent island increases continuously from the second end to the first end.

22. The method of claim 16, wherein the area of the absorbent island is from about 10 cm$^2$ to about 100 cm$^2$.

23. The method of claim 16, wherein the absorbent island comprises a layer of a hydrophilic polyurethane foam.

24. The method of claim 23, wherein the absorbent island further comprises a wicking layer.

25. The method of claim 16, wherein the absorbent island is in the form of a substantially continuous sheet.

26. The method of claim 16, wherein the first end of the absorbent island incorporates a higher fraction of superabsorbent particles than the second end of the absorbent island.

27. The method of claim 16, wherein the first end of the absorbent island has a greater surface area than the second end of the absorbent island.

28. The method of claim 16, wherein the adhesive dressing further comprises a liquid-permeable wound-contacting sheet on a wound-facing side.

29. The method of claim 16, wherein the first end of the absorbent island comprises one or more additional layers of absorbent materials that are not present in the second end of the absorbent island.

30. The method of claim 16, wherein the adhesive-coated backing sheet is semi-permeable.

31. The method of claim 30, wherein the adhesive-coated backing sheet has a moisture vapor transmission rate (MVTR) of approximately 500 to 2,000 $g/m^2/24$ hrs.

32. A method of treating a wound, comprising:
applying an adhesive dressing having an absorbent island attached to an adhesive-coated backing sheet to a wound site;
wherein a width of an adhesive margin is greater in a region of said margin adjacent to a first end of the absorbent island than in a region of said margin adjacent to a second end of the absorbent island; and
wherein the thickness of the absorbent island is greater at a first end than at a second end.

33. The method of claim 32, wherein the thickness of the absorbent island increases continuously from the second end to the first end.

34. The method of claim 32, wherein the absorbent island is substantially triangular, trapezium-shaped, dome-shaped, bell-shaped, or pear-shaped.

35. The method of claim 32, wherein the absorbent island is in the form of a substantially continuous sheet.

36. The method of claim 35, wherein the first end of the absorbent island incorporates a higher fraction of superabsorbent particles than the second end of the absorbent island.

37. An adhesive dressing comprising:
a backing sheet comprising an adhesive coating; and
an absorbent island attached to said backing sheet, said absorbent island having a first end and a second end;
wherein the first end of the absorbent island comprises one or more additional layers of absorbent materials that are not present in the second end of the absorbent island; and
wherein the absorption capacity of the absorbent island is higher at the first end than at the second end.

38. A method of treating a wound, comprising:
applying an adhesive dressing having an adhesive-coated backing sheet and an absorbent island attached to the backing sheet to a wound site such that a first end of the absorbent island is below a second end of the absorbent island when the wound is in its most often-occurring orientation;
wherein the first end of the absorbent island comprises one or more additional layers of absorbent materials that are not present in the second end of the absorbent island; and
wherein the first end of the absorbent island has a greater absorbent capacity than a second end of the absorbent island.

39. A method of treating a wound, comprising:
applying an adhesive dressing having an absorbent island attached to an adhesive-coated backing sheet to a wound site;
wherein a first end of the absorbent island comprises one or more additional layers of absorbent materials that are not present in a second end of the absorbent island; and
wherein the thickness of the absorbent island is greater at a first end than at a second end.

* * * * *